US005731206A

United States Patent [19]
Ledis et al.

[11] Patent Number: 5,731,206
[45] Date of Patent: Mar. 24, 1998

[54] METHOD AND REAGENT SYSTEM FOR ISOLATION, IDENTIFICATION AND/OR ANALYSIS OF LEUKOCYTES FROM WHOLE BLOOD SAMPLES

[75] Inventors: Stephen L. Ledis, Hialeah; Harold R. Crews, Pembroke Pines; Timothy J. Fischer, Plantation; Ted Sena, Miami, all of Fla.

[73] Assignee: Coulter Electronics, Inc., Miami, Fla.

[21] Appl. No.: 630,868

[22] Filed: Mar. 29, 1996

Related U.S. Application Data

[62] Division of Ser. No. 325,531, Oct. 18, 1994, abandoned, which is a continuation of Ser. No. 957,543, Oct. 6, 1992, abandoned, which is a continuation of Ser. No. 611,378, Nov. 13, 1990, abandoned, which is a continuation of Ser. No. 130,911, Dec. 10, 1987, abandoned, which is a continuation-in-part of Ser. No. 025,303, Mar. 13, 1987, abandoned.

[51] Int. Cl.$^6$ ..................................................... G01N 31/00
[52] U.S. Cl. ................................. 436/17; 436/10; 436/18; 436/63
[58] Field of Search ................................. 436/8, 10, 17, 436/18, 63

[56] References Cited

U.S. PATENT DOCUMENTS

| | | |
|---|---|---|
| 3,446,751 | 5/1969 | Weichselbaum . |
| 3,859,098 | 1/1975 | Iwama et al. . |
| 3,872,166 | 3/1975 | Spaenig et al. . |
| 3,874,852 | 4/1975 | Hamill . |
| 3,896,107 | 7/1975 | Klug . |
| 3,941,729 | 3/1976 | Klein . |
| 4,099,917 | 7/1978 | Kim . |
| 4,213,876 | 7/1980 | Crews et al. . |
| 4,250,051 | 2/1981 | Armstrong . |
| 4,269,605 | 5/1981 | Dean et al. . |
| 4,286,963 | 9/1981 | Ledis et al. . |
| 4,324,685 | 4/1982 | Louderback . |
| 4,333,873 | 6/1982 | Shuman . |
| 4,346,018 | 8/1982 | Carter . |
| 4,379,708 | 4/1983 | Rego . |
| 4,436,821 | 3/1984 | Ryan . |
| 4,448,722 | 5/1984 | Crounse . |
| 4,485,175 | 11/1984 | Ledis et al. . |
| 4,629,689 | 12/1986 | Diamond et al. . |
| 4,637,986 | 1/1987 | Brown et al. . |
| 4,751,179 | 6/1988 | Ledis et al. . |
| 4,902,613 | 2/1990 | Chang et al. . |

FOREIGN PATENT DOCUMENTS

| | | |
|---|---|---|
| 1087966 | 10/1980 | Canada . |
| 0068291 | 6/1979 | Japan . |

OTHER PUBLICATIONS

Miale, John B., "Laboratory Medicine Hematology," Third Edition p. 1122, 1967, Published by C.V. Mosby Co.
Schettini, F., Acta Pediat. Scand. vol. 60, 1971."Acid Lysis of Red Blood Cells in Normal Children," pp. 17–21.
Rother, U., Z–Immun.–Forsch., vol. 155, 1978, "Deviated Lysis: Lysis of Unsensitized Cells . . . Low Ionic Strength," pp. 118–129.
DaCosta, A.J., Transfusion, vol. 13, No. 5, 1973, "Effects of Ethacrynic Acid on Human Red Blood Cells," pp. 305–313.
Fisher Scientific Catalog, 1981, p. 299C.

*Primary Examiner*—Marriane P. Allen
*Attorney, Agent, or Firm*—Mitchell E. Alter

[57] ABSTRACT

A lytic reagent composition and a kit of a lytic reagent system are disclosed for the rapid isolation, identification and/or analysis of at least five subpopulations of leukocytes from a whole blood sample. The composition and system have application to any environment in which the study and/or analysis of the leukocyte fraction of whole blood requires their isolation in their native or near native state. The lytic reagent composition of this invention comprises saponin and a carboxylic acid of the formula RCOOH wherein R is H or a $C_{1-3}$ aliphatic hydrocarbon radial optionally substituted by one or more carbonyl and/or hydroxy groups. The kit of a lytic reagent system comprises the lytic reagent composition and a quench reagent.

33 Claims, 3 Drawing Sheets

METHOD AND REAGENT SYSTEM FOR ISOLATION, IDENTIFICATION AND/OR ANALYSIS OF LEUKOCYTES FROM WHOLE BLOOD SAMPLES

CROSS REFERENCE TO RELATED APPLICATION

This is a division of Ser. No. 08/325,531, filed Oct. 18, 1994, now abandoned which is a continuation of Ser. No. 07/957,543, filed Oct. 6, 1992, abandoned, which is a continuation of Ser. No. 07/611,378, filed Nov. 13, 1990, abandoned, which is a continuation of Ser. No. 07/130,911, filed Dec. 10, 1987, abandoned, which is a continuation-in-part of Ser. No. 07/025,303, filed Mar. 13, 1987, abandoned.

BACKGROUND OF THE INVENTION

1. Field of the Invention

This invention is directed to compositions of matter and methods employing one or more of these compositions. More specifically, this invention concerns a novel lytic reagent system for rapidly effecting hemolysis of the erythrocyte fraction of whole blood and thereby permitting the isolation of the leukocyte fraction in its native or near native state. The leukocyte fraction may then be subjected to further study or analysis in a variety of environments. The lytic reagent of this invention consists essentially of a water soluble compound which at least partially dissociates in aqueous media, thereby releasing a proton and a counterion. When the appropriate concentration of such compound is added to a whole blood sample, the extent of dissociation is effective to acidify the sample (pH in the range of from 2.6 to about 4.0), while maintaining the osmolality of the sample below about 100 mOs. One of the preferred uses of this lytic reagent system is the pretreatment of the whole blood sample to effect rapid and essentially complete hemolysis of the erythrocyte fraction. Such pretreatment also results in subtle modification to the leukocyte fraction, thus, facilitating its further differentiation into at least five (5) distinct sub-populations. This reagent system is, thus, suitable for preparation of a whole blood sample for analysis on a focused flow analysis system, such as the VCS whole blood analyzer and the Epics Model C and PROFILE flow cytometer (all of which are available from Coulter Electronics, Inc., Hialeah, Fla.

2. Description of the Prior Art

The separation of complex biological fluids (i.e. whole blood) into its various constituents preliminary to study and analysis of its component parts, is generally desirable and often an essential requirement of many established analytical protocols and/or instrumentation utilized in such studies and analysis. Where such study or analysis of the fluid fraction of the sample is of primary interest, the cellular fraction is separated from the sample without regard for maintaining the cell viability or membrane integrity. Conversely, where the cellular fraction is itself of primary interest to the researcher or clinician, the partitioning of the whole blood sample into its various cellular components requires that the sample treatment/processing techniques be adjusted accordingly. The traditional methods for separation of whole blood samples into its various cellular components is by centrifugation. While this process is effective, it is labor intensive, relatively inefficient and requires physical manipulation of the cellular fraction of the sample.

Where such separation/partitioning of the cellular fraction of the sample is attempted with chemical agents, the results have been less than totally satisfactory for a variety of reasons. More specifically, the vitality and viability of a cell population in vivo or in vitro is dependent upon maintaining a precise physiological environment that is consistent with the preservation of physical cell structure and chemical balance within the cell. This balance is controlled by the permeability and transport characteristics of the cell membrane. Alteration in the physiological environment will in turn evoke a response or change in the cell membrane. The membrane response is "defensive" in nature; that is, the physiological response of the membrane is calculated to maintain the chemical balance within the cell and, thus, its continued and uninterrupted vitality.

It is fully appreciated that such alteration in the ideal physiological environment of the cell can be tolerated only within limits; and, that when such limits are exceeded, permanent injury to the cell can occur. As is further appreciated in the art, such changes in environment (i.e. toxicity of the diluting medium—even with distilled water) can effect hemolysis of the cells.

The degree of tolerance of various cell populations in whole blood to changes in their physiological environment has been extensively studied and documented. The effects of alteration in various aspects of the physiological environment of the cellular fraction of whole blood are both subtle and dramatic and can be effected through dietary metabolites and/or foreign substances. These studies include monitoring the reaction of cellular preparations to different drugs, Da Costa, A. J. et al, Transfusion, (1973), 13, 305; to dietary imbalance, Kobayashi, T. et al, Journal of Biochemistry (1983) 93, 675; and to changes in pH, Rother, U. et al, Z. Immunologie Forschungsgemeinschaft (1978) 155, 118, and Schettini, F. et al, Acta Paediat. Scand. (1971), 60, 17.

In each of the articles noted above, a drug, food metabolite or change in pH resulted in significant alteration in the physiological environment of the blood to the degree where hemolysis of the red blood cells was effected.

More specifically, the above referenced Rother article reports serum activation by acidification (pH 6.4) with hydrochloric acid which lysed unsensitized erythrocytes in the presence of EDTA. The article compares the effect of such acidification with the "deviated lysis" activity observed following serum activation with insulin. An independent and unrelated study by Schettini and his co-workers concluded that red blood cells from infants and young children were more sensitive to acid hemolysis than red blood cells from older individuals.

As of the present, no chemical treatment is available to rapidly and effectively partition a whole blood sample into viable cellular fractions. Where one or more chemical treatments of the whole blood sample is used (as in the preparation or pretreatment of whole blood for the performance of white blood cell differentials), the focus of such treatment has been to alter the sample to permit the differentiation of its cellular components from one another based upon isolation/analysis of (i) the cellular debris (i.e. nuclei) remaining subsequent to such treatment; (ii) the fixation of the cells by such chemical treatments; or (iii) the relatively severe modification of such cells which eventually results in their ultimate disintegration. Such relatively harsh and disruptive chemical treatments of whole blood samples has, however, been successfully applied where combined with relatively sophisticated instrumentation. More specifically, the ability to alter the physiological environment of a cellular population in vitro has been used to advantage in the measurement of certain cellular parameters and to quantitate the individual populations. The distinctive reaction of each individual cell population to a change in its physiological environment has particular advantages in the identification of the individual leukocyte sub-populations of cells of whole blood. The leukocyte population of blood has been classified previously into two major fractions: the lymphoid and the myeloid fraction. The lymphoid fraction consists of lymphocytes (B and T cells). The myeloid fraction consists of monocytes and granulocytes (neutrophils, basophils and eosinophils). One accepted technique for modification of the physiological environment of the cellular population of whole blood has been through the addition of certain so-called "lytic reagents" to a blood sample. The development of certain lytic reagents and lytic reagent systems has provided the clinician with the ability to effectively isolate the white cell population (hereinafter "leukocytes") from the red cell population of whole blood. The relative concentration of leukocytes within the blood sample and the gross morphological appearance of certain classes of these cells can be clinically significant.

This ability to further differentiate the leukocyte population, thus, provides an invaluable diagnostic tool in the study and treatment of various diseases. As is further appreciated, the larger the number of sub-populations of leukocytes which are identifiable, the more accurate and reliable the identification of any one such sub-population.

A number of references have appeared in the recent patent literature which disclose various reagent systems and techniques for enhancing the ability of automated instrumentation to conduct white blood cell differentials. The following references are representative of the pertinent patent literature in this field: U.S. Pat. Nos. 3,874,852; 4,286,963; 4,346,018; 4,485,175; 4,520,274; 4,529,704; and, U.S. applications Ser. No. 615,961, now abandoned, (corresponding International Application PCT/US85/00954, published Dec. 19, 1985); and, Ser. No. 615,966, now U.S. Pat. No. 4,751,179, (corresponding International Application PCT/US85/00868, published Dec. 19, 1985), all of which are hereby incorporated by reference in their entirety. U.S. Pat. No. 3,874,852 (to Hamill) describes a reagent system and method useful in the performance of leukocyte and hemoglobin determinations of whole blood. This reagent system comprises an essentially ferrocyanide free aqueous solution of quaternary ammonium salt and cyanide ions. This reagent system is effective to stromatolyze both red blood cells and platelet cells in whole blood and in the conversion of the free hemoglobin to a chromagen. This system is reported efficacious for leukocyte and hemoglobin determinations with diagnostic accuracy. The leukocyte population profile available with this system is, however, limited to total white cell count, without further differentiation of this cellular fraction into its discrete sub-populations.

U.S. Pat. No. 4,286,963 (to Ledis, et at) describes a lytic diluent and method for achieving rapid lysis of red blood cells in whole blood. This diluent enhances the ability of automated instrumentation to perform differential determinations of lymphoid and myeloid sub-populations of leukocytes and the quantitative determination of hemoglobin. The lytic diluent described by Ledis is composed of a mixture of at least one quaternary ammonium salt and an aryl substituted short chain alkanol in buffered aqueous medium (pH 3.5 to 5.0). The lytic diluent of this Ledis patent is, however, limited in its ability to effect differentiation of the leukocyte population into the two (2) principle sub-populations; namely, the lymphoid and myeloid fractions.

U.S. Pat. No. 4,346,018 (to Carter, et al) describes a multipurpose blood diluent and a method for utilizing this diluent in combination with a weak lysing reagent system for the performance of hemoglobin determination and the differentiation of lymphocytes into the lymphoid and myeloid sub-populations. This diluent comprises, among other constituents, N-(2-acetamido)iminodiacetic acid (ADA) as a blood stabilizing agent. The lysing agent comprises an aqueous solution of at least one quaternary ammonium salt. The diluent/lytic reagent of this Carter patent is, however, limited in its ability to effect differentiation of the leukocyte population into the two (2) principle sub-populations; namely, the lymphoid and the myeloid fractions. In addition, ADA has been found to help stabilize the size distribution, cellular shape, and most importantly, the high degree of cellular dispersion of erythrocytes and platelets to an extent not previously observed with other compounds.

U.S. Pat. No. 4,485,175 (to Ledis, et al) describes a reagent system and method for performance of differential determinations of leukocytes into three (3) sub-populations utilizing automated cell counting equipment. This reagent system comprises a blood diluent and a lysing agent. The lysing agent (comprising an aqueous mixture of quaternary ammonium salts), when added to the diluted blood sample under mild conditions of concentration and at a relatively slow rate, causes unexpected volume modifications to the various leukocyte sub-populations. The discovery which permitted the attainment of the degree of differentiation of the leukocyte population by Ledis, et al is based upon the observation of the relative greater sensitivity of the granulocyte sub-population to lytic agents. By controlling the rate of exposure of the lymphocyte population to lytic agents, the granulocyte sub-population is better preserved. The reagent system of this Ledis et al patent is, however, limited in its ability to effect differentiation of the leukocyte population into three (3) sub-populations; namely, lymphocytes, monocytes and granulocytes.

While all of the above lytic agents and reagent systems facilitate the differentiation of the leukocyte fraction of a blood sample (to a greater or lesser degree), each suffers from a common deficiency; namely, the inability to effect such differentiation without adversely altering the chemical balance of the cells which are subjected to such treatment. Where such alteration in the chemical balance is induced, the effect on the cellular population can range from relatively minor changes (i.e. swelling) to lysis. Dramatic chemical changes in the physiological environment of the leukocyte population also alters the immunochemical response of the leukocyte surface markers. The treatment of leukocytes with such traditional lytic agent system is, thus, inherently incompatible with further immunochemical study of these leukocytes. This limitation has thus, up to now, prevented the use of lytic reagents, alone or in combination with other means, for further refinement in the diagnostic process of various disease states, based upon the differences in the immunochemical response of the respective surface markers of each such cell population.

OBJECTS OF THE INVENTION

Accordingly, it is the object of this invention to remedy the above as well as related deficiencies in the prior art.

More specifically, it is the principle object of this invention to provide a chemical treatment, or pretreatment, of a complex biological fluid sample, such as whole blood, which facilitates the subsequent isolation, identification and/or analysis of one or more cellular populations that are present in the fluid sample.

It is another object of this invention to provide a chemical treatment, or pretreatment, of a whole blood sample which facilitates the partitioning of the sample and thereby the subsequent isolation, identification and/or analysis of the leukocyte fraction based upon the physical, physiological and/or immunochemical properties of such fraction in its native or near native state.

It is yet another object of this invention to provide a chemical treatment, or pretreatment of a whole blood sample which is selective for only one of the cellular constituents of sample.

It is still yet another object of this invention to provide a reagent system which can rapidly and efficiently partition a whole blood sample into an essentially intact leukocyte fraction and a lysed erythrocyte fraction.

It is an additional object of this invention to provide a lytic reagent system for use in differential determination of leukocyte sub-populations of whole blood.

It is another additional object of this invention to provide a novel lytic reagent system which includes both a lytic reagent and a companion quench for use in differential determination of leukocyte sub-populations in whole blood.

It is yet another additional object of this invention to provide a novel lytic reagent system which is effective for use in differential determination of leukocyte sub-populations in whole blood by (a) measurement of physical and/or optical properties of such sub-populations, and/or (b) observation of the immunochemical response or interaction of such sub-populations with immunoreagents (i.e. antiserum) specific for one or more surface markers on each such cell sub-populations.

It is a further object of this invention to provide a method for performance of differential determination of leukocyte sub-populations by both (a) measurement of their physical and/or optical properties, and (b) immunochemical response of such sub-populations to antiserum specific for one or more surface markers on each said sub-populations.

SUMMARY OF THE INVENTION

The above and related objects are achieved by providing a chemical reagent system which is selective in its interactions with the various cellular components of a complex biological fluid sample. This reagent system will, in the various environments contemplated for its use, provide at least one reagent component to effectively alter, on a selective basis, one or more cellular constituents of the complex biological fluid sample to the degree necessary to permit the subsequent isolation, identification and/or analysis of the cellular constituents of interest. This reagent system further contemplates the ability to modulate the chemical treatment of the cellular constituents of the sample by providing a separate reagent which is designed to quench or retard the action of the cell altering reagent on the cellular populations of the sample.

The principles and concepts of this invention have been successfully applied to the treatment of whole blood samples preliminary to whim blood cell differential analysis. The basic components of the chemical reagent system of this invention include a "lytic reagent" and a companion reagent for the lytic reagent referred to as a "quench." The primary functions of the quench are to retard the activity of the lytic reagent and to restore the ionic balance of the sample subsequent to its treatment with the lytic reagent.

The lytic reagent system and method of this invention, thus, has as its broadly stated objectives, the selective hemolysis of the erythrocyte population of a whole blood sample, while facilitating the subsequent isolation, identification and/or analysis of one or more of the leukocyte sub-populations of the same sample, based upon one or more physical, physiological and/or immunochemical characteristics which are indicative of the sub-population of interest.

The lytic reagent of this invention consists essentially of a water soluble compound which at least partially dissociates in the aqueous media, thereby releasing a proton and a counterion. When the appropriate concentration of such compound is added to a whole blood sample, the extent of dissociation of such compound is effective to acidify the sample (pH in the range of from 2.6 to about 4.0), while maintaining the osmolality of the sample below about 100 mOs. There are at least three (3) classes of compounds which have been found suitable as lytic reagents for achieving the objectives of this invention. These classes include low molecular weight carboxylic acids, sulfonic acids and activated phenols.

The carboxylic acids suitable as lytic reagents of this invention can be represented by the following formula

R—COOH wherein R is H, an aliphatic hydrocarbon radical having from 1–3 carbon atoms; a carbonyl substituted aliphatic hydrocarbon radical having from 1–3 carbon atoms; a hydroxy substituted aliphatic hydrocarbon radical having from 1–3 carbon atoms; or an aliphatic hydrocarbon radical having from 1–3 carbon atoms and multiple carbonyl and/or hydroxy substituents.

Representative carboxylic acids within the foregoing formula include formic acid, methane-carboxylic acid, (acetic acid), 2-hydroxy-ethane-2-carboxylic acid (lactic acid); 1,2-ethane-dicarboxylic acid (succinic acid); and 2-hydroxy-1, 2,3-propane-tricarboxylic acid (citric acid); and their respective mixtures.

The sulfonic acids suitable as lytic reagents of this invention can be represented by the following formula

R—SO₃H wherein R is hydroxy, an aliphatic hydrocarbon radical of 1–3 carbon atoms or aryl.

Representative sulfonic acids within the foregoing formula include sulfuric acid; methanesulfonic acid; ethanesulfonic acid; benzenesulfonic acid; p-toluenesulfonic acid; nitrobenzenesulfonic acid, and their respective mixtures.

The activated phenols suitable as lytic reagents of this invention can be represented by the following formula

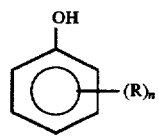

wherein R is an electron withdrawing group such as halogen, cyano, nitro or any combination of such electron withdrawing substituents; and n is 1–3.

Representative activated phenols within the foregoing formula include para-nitrophenol; meta-nitrophenol; ortho-nitrophenol; 2,4-dinitrophenol; para-chlorophenol; para-cyanophenol; and 1-chloro-2,4-dinitrophenol; and their respective mixtures.

The foregoing are representative of the classes of materials which can be used as lytic reagents consistent with the objectives of this invention. It is appreciated that the relatively weak acids will exist as both an undissociated compound and in the dissociated state within the sample. Strong acids are, of course, essentially completely dissociated in the sample. Certain undissociated acid and the counterions from the dissociated acids can apparently influence the degree of differentiation of the leukocyte fraction, depending upon their relative concentration in the sample and the physiological recognition (if any) of the acid and/or its counterion by the cellular analytes of interest. For example, phosphoric acid, even at the appropriate pH, is generally not acceptable to achieve differentiation of the leukocyte into five (5) sub-populations. It is hypothesized that counterion compatibility (phosphate ion) is unacceptable and, thus, differentiation of the leukocyte population is decidedly more difficult.

In this preferred embodiment of the concepts of this invention, the novel lytic reagent system comprises an aqueous solution containing a differentiation effective amount of lytic reagent selected from the group consisting of formic acid, acetic acid and their respective mixtures. In these mixtures, the formic acid will preferably comprise the major functional component with the acetic acid being present in only minor amounts. The phrase "differentiation effective amount" is used throughout this disclosure as indicative of a concentration of lytic reagent which is not only effective for lysing red blood cells, but also effects subtle changes in the leukocyte cell fraction to facilitate the subsequent isolation, identification and/or analysis of this leukocyte cellular fraction; including the ability of instrumentation to perform differential analysis and identification of at least five (5) sub-populations of leukocytes. The preferred range of concentration of formic acid in the lytic reagent is in the range of from about 0.10 to about 0.25% (v/v). The concentration of such preferred lytic reagent which has been determined as satisfying the foregoing criteria is from about 0.009 to about 0.020 milliliters of formic acid per milliliter of whole blood. This subtle modification of the leukocyte fraction by the lytic reagent is achieved while preserving the immunochemical response of the surface markers of each of the five (5) cell sub-populations of leukocytes. As stated previously, it is the primary objective in this treatment of the whole blood sample with the lytic reagent, that such reagent effectively accomplishes stromatolysis of the erythrocyte cell fraction while preserving the leukocyte fraction in its essentially native state.

In one of the preferred embodiments of this invention, the reagent system can contain saponin in addition to the lytic reagent. The term "saponin" is intended as referring to commercial grade quillaja saponin powder. The addition of saponin to the reagent system is optional and generally only appropriate where the clinician is monitoring certain parameters of the leukocyte sub-populations other than by photo-optical or immunochemical techniques. The addition of appropriate quantities of saponin to the lytic reagent system is effective in its ability to reduce the size of red cell fragments so as to prevent their interference in determination of certain leukocyte parameters by measurement of electrical opacity and/or Coulter volume utilizing the techniques described in Coulter U.S. Pat. Nos. 2,656,508 and 3,502,974 (which are hereby incorporated by reference in their entirety). The preferred range of concentration of saponin which has been determined as effective for reducing red cell fragments is from about 0.006 to about 0.012 grams per milliliter of whole blood. In brief, the technique involves the measurement of cell volume utilizing radio frequency current (RF) and DC field excitation. By generating a particle sensing field with both a low frequency or direct current (DC) and radio frequency (RF) current excitations, two or more interrelated output signals can be derived from passage of a single particle (i.e. leukocyte) through an electric field. The value derived from this output signal is termed "relative opacity", which is unique for each sub-population of leukocyte. The addition of saponin to the lytic reagent reduces the size of the red blood fragments to a point where they will not interfere with or themselves cause, the derivation of an output signal indicative of a species of leukocyte.

Where cell differentiation is based upon light scatter measurements, (utilizing the techniques described in Fulwyler U.S. Pat. No. 3,989,381 and/or Auer, et al U.S. Pat. No. 4,038,556—which are hereby incorporated by reference in their entirety), the red cell fragments do not interfere or adversely effect the photometric differentiation of the various sub-populations of leukocytes. Thus, the addition of saponin to the lytic reagent system is unnecessary where such differentiation is based upon photometric analysis.

The amount of time of exposure of the blood sample to the lytic reagent system is critical to the differentiation method of this invention. This exposure period, as illustrated in the Examples disclosed hereinafter, should not exceed ten (10) seconds, and most preferably, requires only about six (6) seconds or less. Both of these exposure times are specified for room temperature (~18°–28° C.). In each instance, the action of the lytic reagent is quenched by simple addition of appropriate concentrations of salts to the sample to return the cells to their native physiological environment. The quench effectively retards further activity of the lytic reagent upon the leukocytes without need for the addition of fixatives. The quench for the lytic reagent is an essential complement to the lytic reagent system where subsequent analysis of the leukocyte fraction requires retarding the activity of the lytic reagent. The leukocytes are stabilized by this quench by controlling the pH within a fairly narrow range (pH ~6.00 to 7.25) and osmolality (~300 to 330 milliosmoles). The quench can also be formulated to match the conductivity of a chosen "sheath" fluid which is utilized in a focused flow aperture analysis system. The composition and volume of the quench is adjusted to provide optimal separation of the five (5) major leukocyte subclasses when analyzed in accordance with the techniques (RF frequency current in combination with DC field excitation) described in Coulter, et al U.S. Pat. No. 3,502,974 (previously incorporated by reference). The leukocyte fraction of the sample, treated in the above manner, can be readily differentiated to at least five (5) sub-populations by a hematology analyzer capable of multiple parameter particle (cell) measurements; and, by immunochemical interaction with antiserum (i.e. antibodies, binding proteins, etc.) that are specific for one or more surface markers on the cells of each such cell sub-population.

Figure 1:
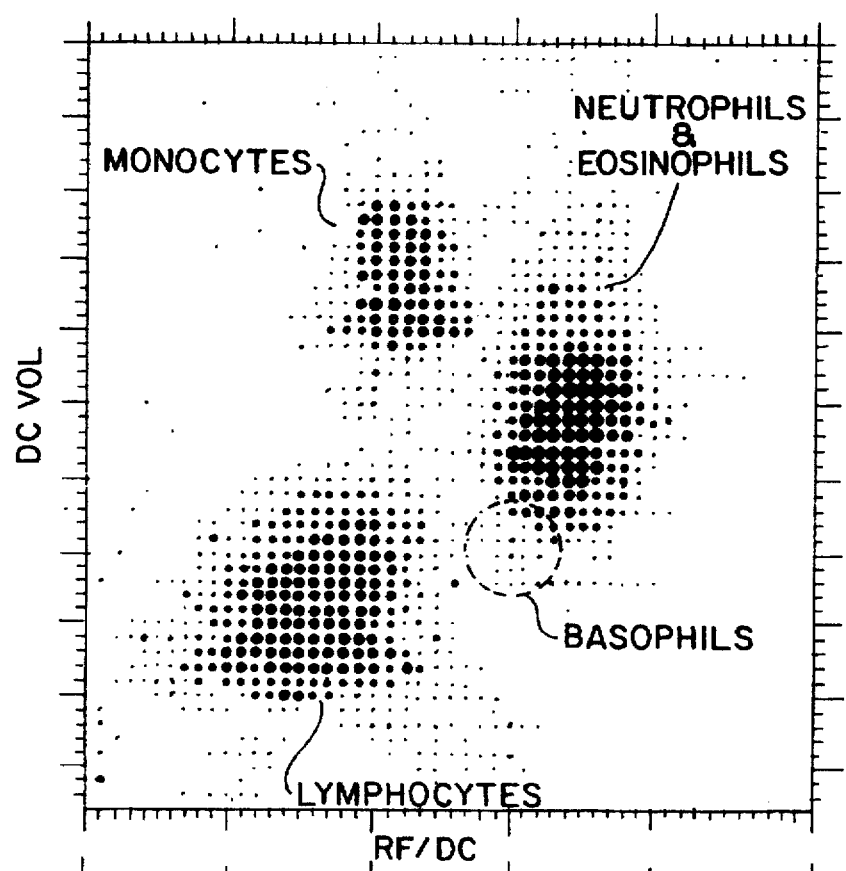
FIGS. 1, 2 and 3 are scattergrams representing the white cell differential analysis of the blood sample of Example II; the X-axis of each such Fig. being different from one another.

DESCRIPTION OF THE INVENTION
INCLUDING PREFERRED EMBODIMENTS

The lytic reagent system of this invention comprises an aqueous solution containing surprisingly low concentrations of the lytic reagent (preferably less than 1.0% by volume). The lytic reagent of the reagent system of this invention can generally be described as a water soluble, acidic compound which at least partially dissociates in aqueous media. As noted above in the Summary of the Invention, a number of interrelated factors are believed to be essential for such compounds to perform within the various environments contemplated for this invention. These factors include pH, osmolality and counterion compatibility. The acidification of the sample is necessary to effect the desired lysis of the erythrocytes. Where, however, the pH of this sample departs from the preferred range of from about 2.6 to about 4.0, the ability to differentiate the leukocyte fraction into five (5) distinct subpopulations is apparently compromised.

This ability to effectively differentiate the leukocyte population into its various subpopulations is also hindered where the osmolality of the lysed sample is not maintained below about 100 mOs. Accordingly, where either pH or osmolality of the lysed sample is not maintained within the foregoing parameters, the ability to effectively differentiate between the various subpopulations of leukocytes is significantly impaired.

The counterion of the dissociated acidic compound has, in certain instances, been shown to effect the degree to which differentiation of the leukocyte fraction can be effected. For example, phosphoric acid, even at concentrations which produce the appropriate pH and osmolality, is not (as) effective in the differentiation of this leukocyte fraction into its various subpopulations. It is hypothesized that the counterion of this acid (phosphate) interacts in some unknown manner or fails to interact with the leukocyte fraction, and thereby does not afford the extent of differentiation afforded by other water soluble, acidic compounds.

There may also be other factors and mechanisms which are inherent in the action of the lytic reagents upon the sample which account for the surprising and unexpected results of this invention. As of the present, only the above three (3) enumerated variables have been identified; and it is not intended to imply that there may not be others or that this invention is dependant upon only the above identified variables for its effectiveness.

The lytic reagent of this invention is preferably an aqueous solution of formic acid, acetic acid or mixtures of formic and acetic acid in which formic acid is the predominant functional component. This aqueous solution is prepared by simple addition of the lytic reagent to deionized water. The amount of lytic reagent added to this diluent is sufficient to prepare a solution containing from about 0.05 to about 0.5% (v/v) solution. In the preferred embodiments of this invention, the concentration of lytic reagent will range from about 0.1 to about 0.25% (v/v).

Where the lytic reagent comprises a mixture containing both formic and acetic acid, the acetic acid is preferably only present as a partial replacement for a definitive amount of formic acid and then only at a concentration in the range of from about 0.05 to 0.10% (v/v).

The lytic reagent system also optionally can contain very small amounts of saponin (preferably at least about 0.05 up to about 0.2 weight percent) in addition to the lytic reagent. As is fully appreciate, the effectiveness of saponin, as a lytic reagent, is highly concentration dependent. If saponin is used at low concentrations, it is generally ineffective for this purpose. Were saponin to be used as a lytic reagent, it would have to be present in concentrations of at least 2.0 weight percent, or more, to effect essentially complete stromatolysis of the red blood cells. Unfortunately, the saponin, where present at a lytic effective concentration, can also cause lysis of white blood cells. Thus, any changes induced in the white blood cell population utilizing saponin as the lytic agent, and their subsequent differentiation by automated instrumentation must be based upon whatever discernible and distinctive characteristic of their respective nuclei. Its presence in the lytic reagent system of this invention is, however, desirable where the clinician is concerned with so-called "ghosts" (intact red cell membranes) interfering with differential measurements based upon distinctions in physical and/or electrical properties. As noted previously, saponin would not be a necessary addition to the lytic reagent system if the differential measurements where made by purely photooptical instrumentation and/or by immunochemical analysis.

The lytic reagent system can also contain other traditional additives, to the extent their presence is not otherwise incompatible with the primary functional components of the system (i.e. anti-microbial preservatives, such as sodium omadine.

The lytic reagent system of this invention can be combined with a whole blood sample by simple manual or automated addition, the lytic reagent and sample allowed to briefly interact, and the action of the lytic reagent substantially retarded by addition of a suitable quench. The quench, to be effective in this environment, must, thus, be capable of retarding the lytic activity of the lytic reagent immediately upon its addition to the aqueous mixture contained in the blood sample and the lytic reagent. The precise formulation of the quench can vary, depending upon the composition of the lytic reagent system and the sheath fluid used in a focused flow aperture analysis system. The quench is typically an aqueous solution containing soluble salts which are both effective to substantially retard and/or substantially neutralize the lytic activity of the lytic reagent and restore the ionic balance to the sample. This restoration of the ionic balance will extend the longevity of the surviving cells and permit subsequent analysis on equipment which requires that the sample be electrically conductive (contain electrolytes), as for example with a Coulter Counter® whole blood analyzer.

A quench which is suitable for use in conjunction with a lytic reagent composition of this invention can, and usually will, contain any combination of at least two of the following four ingredients: sodium chloride, sodium sulfate, sodium bicarbonate, sodium carbonate; and, in addition, sodium azide as a preservative. The effectiveness of the quench upon the lytic reagent in the context of this invention is determined by its ability to rapidly reduce the lytic activity of the carboxylic and non-volatile mineral acids selected for use in the lytic reagent system. As noted above, the method and equipment utilized in the differentiation of the leukocyte sub-population can also place certain requirements (i.e. conductivity, pH, etc.) upon the precise formulation of the quench. More specifically, when such differentiation is performed in a focused flow aperture analysis system, the composition and volume of quench can be critical to optimal separation (differentiation) of the five (5) leukocyte subclasses from one another. In this type of analysis system, the ionic balance of the quench must also be adjusted to obtain a satisfactory conductivity match of the lysed blood sample to the sheath fluid. In the preferred quench formulation, the major ionic species and their relative ratio in the lysed-quenched blood sample should be essentially the same as the major ionic species and their relative ratio in the sheath fluid. The relative concentration of the functional components of the quench, which is to be used in conjunction with the lytic reagent system of this invention, will range from about 1 to about 3% (w/v) sodium chloride, about 0.25 to about 0.8% (w/v) sodium carbonate or bicarbonate, and about 2 to about 4% (w/v) sodium sulfate. The precise relative quantities of ingredients of the optimum quench are generally determined empirically; the objectives of such adjustment being to attain the pH of the lysed blood sample within the range of from about 6.0 to about 7.5, and a final osmolality of the stabilized lysed blood sample in the range of from about 300 to about 330 mOs. It has been previously observed, in a focused flow aperture system, that optimal clustering of the leukocyte subclasses is achieved by adjustment in the osmolality of the final blood sample to about 310 mOs. The essentially complete neutralization of the acidity of the lysed sample with an alkaline quench can be critical to a focused flow aperture analysis system. Components of the sample (i.e. fibrin and platelets) are pH sensitive and can form aggregates under acidic conditions which can potentially interfere with differential analysis (i.e. noise) or physically obstruct the aperture of a focused flow aperture system.

It is not contemplated, nor intended, that the quench also necessarily inhibit or neutralize the saponin (when present). The reasons for this are quite simple, in that the saponin, at the concentrations contemplated (~0.2 weight percent), is relatively ineffective as a lytic reagent. If the quench were to also inhibit the saponin activity upon its addition to the sample, adequate clarification of the sample (destruction of intact red blood cell membranes) would not take place. Thus, it is anticipated that the activity of the saponin continue of from about 5 to 15 seconds subsequent to quenching of the activity of the lytic reagent. It may, under some circumstances, be appropriate to provide an independent quenching agent for the saponin; however, at the concentrations presently contemplated, (less than 0.1%) none would appear necessary to achieve or further the objectives of this invention. The adequacy of the quenching agent is, of course, based upon certain assumptions relating to sensitivity of cells of sample (analytes of interest) to the lytic reagent and the period of contact of the lytic reagent and these cellular analytes prior to analysis. As noted above, the quench retards the lytic activity, it does not totally eliminate its effect upon the leukocyte fraction of the sample. Thus, if a substantial period of time is to elapse between addition of quench and analysis of the sample, it may be desirable to fix the leukocyte fraction to preserve the characteristic size and shape of the cellular analytes of interest.

In the preferred embodiments of this invention, the duration of effective contact of the lytic reagent and the blood sample (from the time the two are combined, to the time when the quench is added), must be less than ten (10) seconds, and most preferably six seconds or less. The interval of reactive contact of the lytic reagent and blood sample as specified above, presumes such reactive contact occurs at room temperature (~18°–28° C.). Of course, if the temperature is in excess of this level, the period of reactive contact would be somewhat less and vary inversely; and, if the temperature is lower than this level, the period of reactive contact would be somewhat longer. It is both critical and essential to the successful performance of the differential method of this invention, that the kinetics of the interaction of the lytic reagent upon both the sacrificial cell population (red blood cells) and the desirable cell fraction (leukocytes) be controlled carefully and precisely. The mechanism by which the lytic reagent reacts with both cell fractions is not known with precision, only the manifest effect of such interaction. It is, thus, beyond the scope of this discussion to speculate how these improvements in differential analysis are attained and, thus, no attempt is made herein to explain or later claim such mechanism.

By limiting the exposure of both these cell fractions to the lytic reagent, stromatolysis of the erythrocytes is effectively and efficiently accomplished, while additional subtle changes are induced in the leukocytes by the quench to enable their effective differentiation. Both of these events occur essentially concurrently, while preserving the native immunochemical reactivity of the differentiated leukocyte fraction.

As noted above, the duration of contact of the lytic reagent with the blood is sufficient to effect a selective destructive response of the sacrificial cell fraction, while at the same time effecting a differential response in the leukocyte fraction; such changes unexpectedly permitting the physical differentiation of at least five (5) cell sub-populations of leukocytes from one another. The lytic reagent, in sharp contrast to the more traditional types of lyse (i.e. saponin, quaternary ammonium salts), does not detrimentally alter the native immunochemical response of the surface markers of each of the cells within the leukocyte sub-populations. This quality is believed to be unique to the lytic reagents of this invention.

Blood samples which have been exposed to the above lytic reagent system can be subjected to differential measurement on instrumentation designed for this purpose. Such differentials can be performed on a device utilizing technology of the type described in U.S. Pat. Nos. 3,549,994 (which is hereby incorporated by reference in its entirety), 3,502,974 and 3,989,381. Features of the inventions described in the above referenced patents can be embodied into commercially practical instrumentation. In brief, the blood sample is initially treated by mixing with the lytic reagent system, utilizing automated pipetting equipment. The lytic action of the lytic reagent on the sacrificial cell population (red blood cells), must be both rapid and effective. A quench then is added by similar pipetting means to substantially retard the activity of the lytic reagent upon the surviving cell fraction (leukocyte). The sample containing the leukocyte fraction then is subjected to counting of each of the individual cell sub-populations, and/or histograms and/or scattergrams generated from the data collected in this fashion.

The principle involved in performance of Coulter volume measurements is well known to those skilled in the art as the "Coulter Principle." In brief, the operation of instrumentation utilizing the Coulter Principle involves the measurement of change in the impedance caused by the passage of individual cells through a sensor designed to detect a voltage drop caused by the presence of the cell. The instrumentation utilizing this principle comprises two fluid vessels or chambers, each containing a conductive electrolyte solution. At least two electrodes having opposite polarity are immersed in the electrolyte solution, with each fluid compartment having one of the electrodes disposed therein. A sample of the electrolyte solution, having the blood cells suspended therein, is passed through a constricted fluid path, or orifice, interposed between the two fluid compartments. Although the constricted pathway can take different forms, in each device such path defines a sensing zone wherein the presence or absence of a particle gives rise to a detectable change in electrical characteristics of the path. For example, relatively poorly conductive blood cells passing through this path, displace a volume of electrolyte solution equal to the cell volume, causing a voltage drop by increasing the path impedance. The resistance pulses defined by the drops in voltage are used for particle counting and particle volume determination. The Coulter principle is more fully described in U.S. Pat. No. 2,656,508. This technique for sensing and identifying specific cell populations can be enhanced by a combination of Coulter principle measurements with radio frequency excitation of the cells within the sensing zone. In brief, this radio frequency enhancement operates upon the principle that a particle moving through the sensing zone of a hematology analyzer will cause a phase shift in radio frequency (RF) energy within the sensing zone. This shift in phase can be correlated with physical and compositional characteristics of a cell population. This technique for RF differentiation of cells is more fully described in U.S. Pat. No. 3,502,974. White cell differentiation also can be achieved utilizing optical measurement principles of flow cytometry as described in U.S. Pat. No. 3,380,584 (which is hereby incorporated by reference in its entirety).

The lytic reagent system of this invention is effective to induce subtle changes in the leukocyte cell fraction to enhance the differentiation of five (5) distinct sub-population of leukocytes on automated cell counting equipment, see for example, U.S. Pat. No. 4,412,004 (to Ornstein, et al—which is hereby incorporated by reference in its entirety). These five (5) distinct sub-populations, as noted previously, include: lymphocytes, monocytes and three species of granulocytes (eosinophils, basophils and neutrophils). Each of these sub-populations of leukocytes have distinctive surface markers. In certain disease states, the surface markers on one or more of these sub-populations will provide a unique immunochemical response and, thus, make diagnosis or confirmation of disease possible at an early stage of its development. The detection of these distinctive surface markers on one or more of these sub-populations of leukocytes will, of course, be dependent upon the ability to effectively physically isolate these cells having characteristic disease state surface markers from the non-effected cells; and, the relative concentration of the effected cells within the sample being analyzed.

The initial lytic conditions contemplated by this invention permit an extension in the longevity of the cell populations which survive and which are to be differentiated from one another. For the most part, it is anticipated that cell longevity of at least seventy-two (72) hours would be appropriate for certain types of immunochemical analysis. In certain applications of this differential method, it may be both necessary and appropriate to maintain one or more of these sub-populations in vitro for several hours, or possibly even several days. In order to achieve such extended stability, it is advisable to physically separate the leukocytes from the fluid fraction containing the lytic reagent/quench mixture and, thereafter, resuspended such cells in a physiological medium.

The following examples are provided as illustrative of the unique advantages of the lytic reagent system of this invention. The equipment and techniques utilized in the preparation and evaluation of this lytic reagent system are standard or as hereinbefore described. Parts and percentages appearing in such Examples are by weight unless otherwise stipulated.

EXAMPLE I

Figure 4:
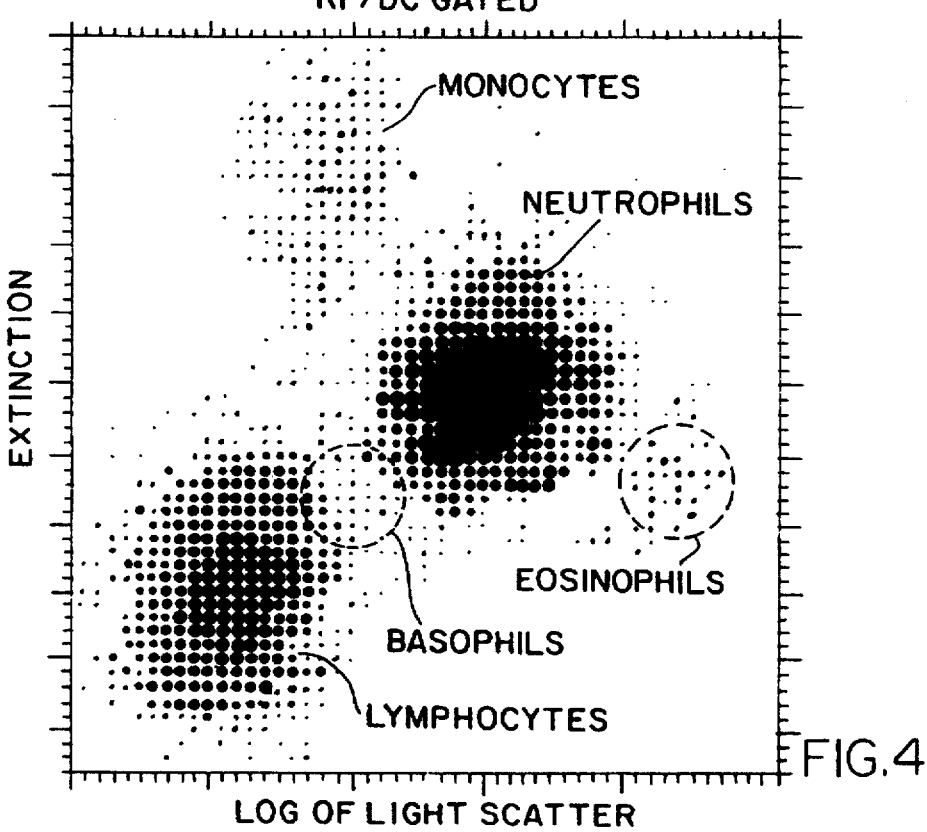
FIG. 4 is a scattergram representing the white cell differential analysis of the blood sample of Example I.

The lytic reagent system of this invention was prepared from reagent grade chemicals. A 0.12% (v/v) formic acid solution was initially prepared by combining 1.3 ml of 90% formic acid and 998 ml deionized water. A 50 uL whole blood sample ($K_3$ EDTA) and 800 microliters of 0.12% formic acid solution are gently mixed by swirling the two together for five (5) seconds at room temperature (~20° C.). The lytic action of the formic acid arrested after about 5 seconds, by the addition of 400 ul of a quench solution containing 0.55% sodium bicarbonate, 3.0% sodium chloride and 0.01% sodium azide. The sample was adequately quenched and ready for differential analysis by flow cytometry techniques within about 5 to 10 seconds subsequent to the addition of the quench. The equipment used in such differential analysis was equipped with a helium/neon laser and silicon diode detectors for measurement of light scatter. The leukocytes are observed and their individual parameters determined by optical parameter analysis, i.e. measurement of light extinction (zero angle scatter), and any one of several angular ranges of light scatter. The scattergram of the sample generated in the above manner is illustrated as FIG. 4. Five (5) distinct sub-populations of leukocytes are identified and quantified in this scattergram.

EXAMPLE II

The procedures of Example I are repeated, except for the addition of 0.05% (w/v) saponin powder to the aqueous solution containing 0.12% formic acid. The whole blood sample (50 microliters) is then combined (as previously described) with 600 microliters lytic reagent. The lytic reagent is quenched after 6 seconds by addition of 265 microliters of an aqueous solution containing 0.60% sodium carbonate, and 3.00% sodium chloride.

The addition of saponin to the lytic composition effectively eliminates interference of the red cell debris from Coulter volume measurements. The effectiveness of the saponin is highly temperature dependent. The essentially total elimination of interference from red cell debris requires an additional 10 seconds (at room temperature ~18° to 28° C.) subsequent to completion of lysing the red cell fraction of the sample. In the event the sample is maintained at a lower temperature (below 18° C.), a somewhat longer period will be required to effectively eliminate interference from the red cell debris by the saponin.

The sample was ready for differential analysis within about 10 to 20 seconds subsequent to the addition of the quench. The sample was subjected to photo-optical measurement as described in Example I. Leukocytes in the sample were also observed by measurement of DC and RF volumes using an ISOTON® II sheath fluid and the resultant scattergram is illustrated in FIG. 1. Four distinct sub-populations of leukocytes were identified and quantified in the simultaneously obtained light scatter vs. DC scattergram of FIG. 2. A fifth sub-population of leukocyte (basophils) is isolated by generation of a "gated" secondary scattergram. This basophil population is depicted in the scattergram illustrated in FIG. 3.

EXAMPLE III

The procedures of Example II are repeated, utilizing the same formic acid/saponin reagent composition. The lytic activity of the formic acid is arrested with a quench containing 3.13% (w/v) sodium sulfate (anhydrous), 1.45% (w/v) sodium chloride and 0.60% (w/v) sodium carbonate (anhydrous). The sample was analyzed by electro-optical techniques in the manner described in Example II and the scattergram results were similar to that of FIGS. 1, 2 and 3. The sheath fluid was, however, changed to ISOTON® III diluent.

EXAMPLE IV

The procedures of Example III were repeated, except for use of a concentrated lysed-quenched blood sample for more rapid data acquisition. The lytic reagent comprises 0.15% (v/v) formic acid and contains 0.10% (w/v) saponin powder.

The lytic activity of the formic acid was arrested by a quench containing 2.67% (w/v) sodium sulfate (anhydrous), 1.24% (w/v) sodium chloride and 0.56% (w/v) sodium carbonate (anhydrous).

Figure 2:
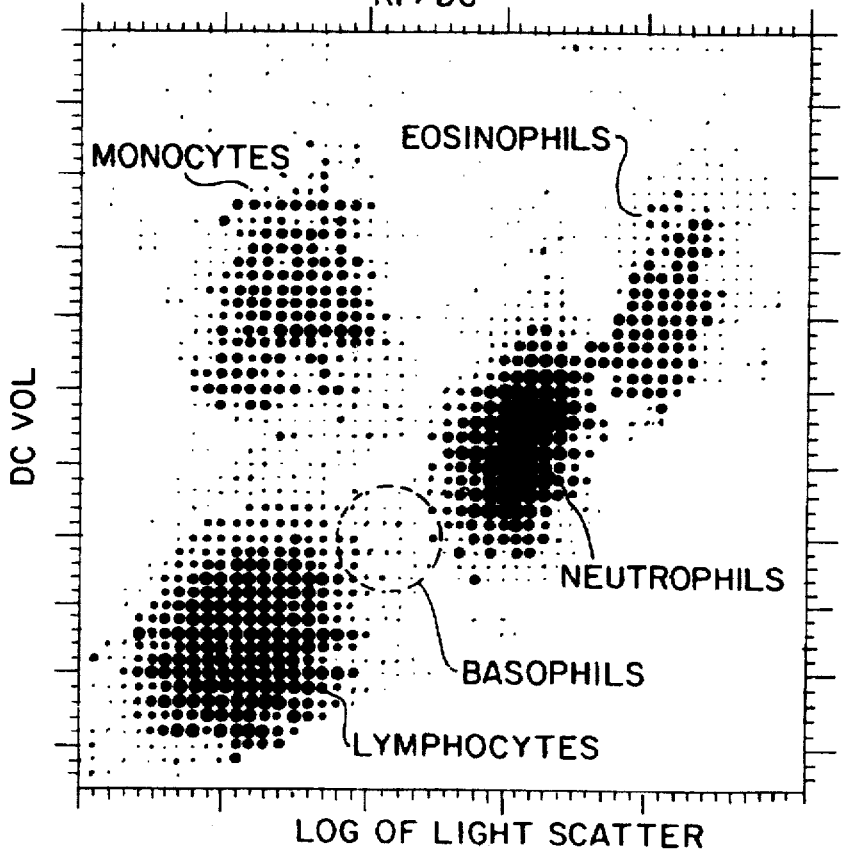
Figure 3:
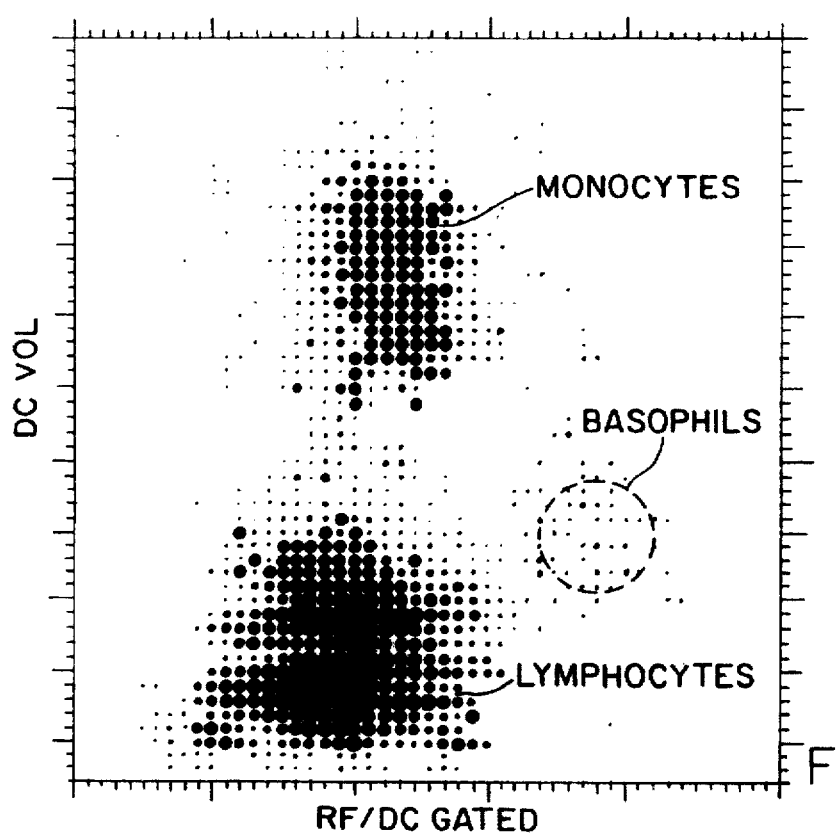

This differential analysis was performed by addition of 50 microliters whole blood to a glass culture tube containing 300 microliters lyse reagent. The sample and lyse are mixed by swirling the contents of the tube for approximately 6 seconds and the lytic activity of the formic acid arrested by addition of 165 microliters of the above quench. The sample was then subjected to electro-optical measurement in the manner described in Example II and the resultant differential analysis was comparable to that of Example II. (as illustrated in FIGS. 1, 2 and 3).

EXAMPLE V

Figure 5:
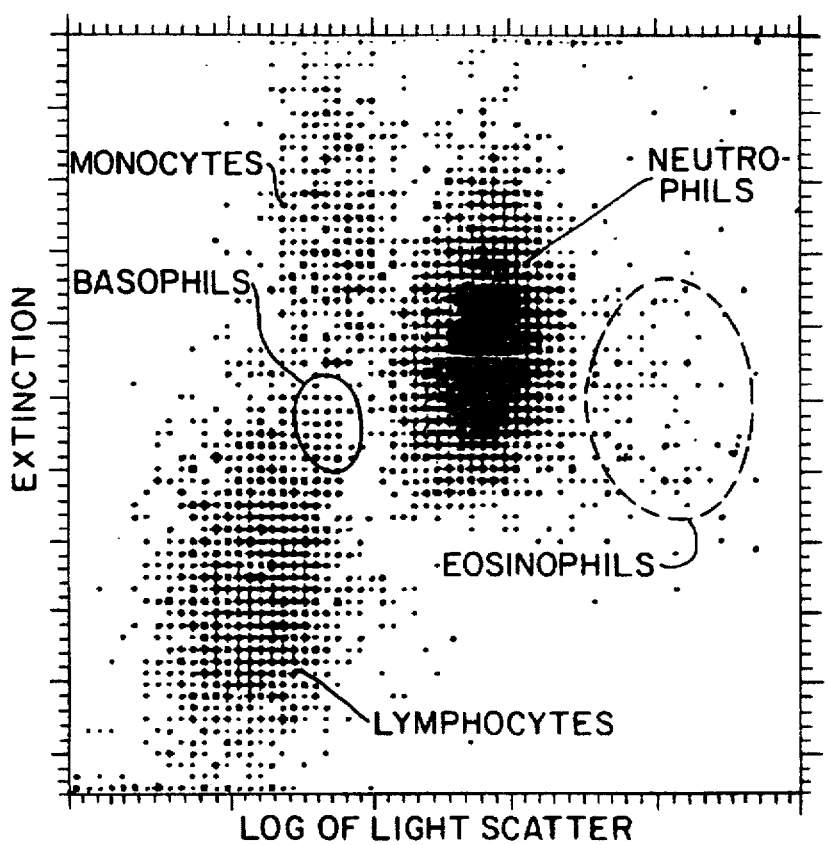
FIG. 5 is a scattergram representing the white cell differential analysis of the blood sample of Example V.

The procedures of Example I were repeated, except for the substitution of 0.1% (v/v) acetic acid for the formic acid in the lytic reagent system. The lytic activity of the reagent was arrested, after approximately 5 seconds, with a quench comprising 0.25% sodium bicarbonate in 2.0% sodium chloride solution. The sample was adequately quenched and ready for differential analysis by flow cytometry techniques within about 5 to 10 seconds subsequent to the addition of the quench. The equipment and analytical techniques used in such analysis were essentially the same as in Example I. The differential analysis performed on this sample is illustrated in the scattergram of FIG. 5.

EXAMPLE VI

Figure 6:
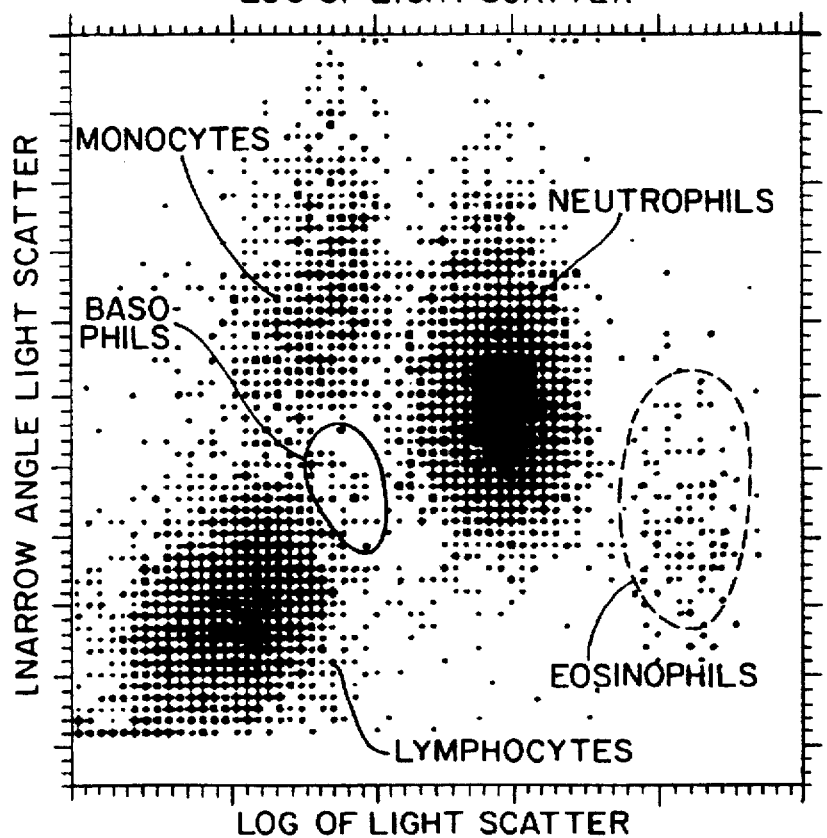
FIG. 6 is a scattergram representing the white cell differential analysis of the blood sample of Example VI.

The procedures of Example V were repeated except for extending the period of contact of the sample and the lytic reagent from 5 to 7 seconds prior to the addition of the quench. The quench was also modified slightly by increasing the concentration of sodium bicarbonate from 0.25% to 0.375% in the 2.0% sodium chloride solution. The results of this differential analysis of the leukocyte population are illustrated in the scattergram of FIG. 6.

EXAMPLE VII

The procedures of Example I are repeated, except for the separation and identification of the various sub-populations of leukocyte by immunochemical techniques. Once the action of the lytic reagent is quenched, the sample is diluted with an isotonic buffer and sequentially slurried with a series of magnetic particles, each of which having been pre-treated with a different antiserum specific for adsorption of only one species of leukocytes. The adsorbed cells can be separated sequentially from the sample using the conventional magnetic particle separation techniques described in the previously incorporated references. The separated particles can then undergo additional screening for surface markers which are indicative of one or more disease states.

EXAMPLE VIII

The procedures of Example VII are repeated, except that the cells are separated from the magnetic particles and cultured with an immortal cell line in accordance with the procedures of Kohler and Milstein, Nature, Vol. 256, 495–497 (1975). The clones produced in this fashion are screened for the production of antiserum specific for the surface marker of interest.

EXAMPLE IX

The procedures of Example V are repeated, except for the substitution of 0.1% (v/v) citric acid for the acetic acid in the lytic reagent system. This substitution achieved results comparable to that attained in Example V.

EXAMPLE X

The procedures of Example V are repeated, except for the substitution of 0.1% (v/v) succinic acid for the acetic acid in the lytic reagent system. This substitution achieved results comparable to that attained in Example V.

EXAMPLE XI

The procedures of Example V are repeated, except for the substitution of 0.1% (v/v) lactic acid for the acetic acid in the lytic reagent system. This substitution achieved results comparable to that attained in Example V.

EXAMPLE XII

The procedures of Example V are repeated, except for the substitution of 0.05% (v/v) sulfuric acid for the acetic acid in the lytic reagent system. This substitution achieved results comparable to that attained in Example V.

The foregoing Detailed Description and Examples are intended as illustrative of some of the preferred embodiments of the lytic reagents, reagent systems and methods of this invention. It is not the intent of the inventors that these specific embodiments of their invention be interpreted as indicative of the scope or breadth thereof, but rather simply supportive of the claims which are set forth hereinafter.

What is claimed is:

1. A lytic reagent composition for selective chemical treatment of a whole blood sample, said lytic reagent composition comprising saponin and a lytic reagent, wherein said lytic reagent is a carboxylic acid of the formula RCOOH or a sulphonic acid of the formula R'SO$_3$H;

wherein R is H or a C$_{1-3}$ aliphatic hydrocarbon radical optionally substituted by one or more carbonyl and/or hydroxy groups, and R' is OH, a C$_{1-3}$ aliphatic hydrocarbon radical or aryl; and wherein the relative concentration of the lytic reagent composition is in an effective amount to effect partitioning of a whole blood sample into a lysed red cell fraction and an essentially intact leukocyte fraction in such a state as to allow differential analysis of at least five sub-populations of such leukocytes.

2. The lytic reagent composition of claim 1, wherein the concentration of the lytic reagent is from about 0.01 to about 1.0 percent by volume.

3. The lytic reagent composition of claim 2, wherein the concentration of the lytic reagent is from about 0.05 to about 0.5 percent by volume.

4. The lytic reagent composition of claim 1, wherein the saponin is in an amount effective to reduce the size of red blood cell fragments so that they will not cause a derivation of an output electrical signal indicative of a species of leukocyte.

5. The lytic reagent composition of claim 1, wherein the saponin is in an amount from about 0.05 to about 0.20% by volume.

6. A lytic reagent composition for selective chemical treatment of a whole blood sample, said lytic reagent composition comprising saponin and a lytic reagent, wherein said lytic reagent is a carboxylic acid of the formula RCOOH or a sulphonic acid of the formula R'SO$_3$H;

wherein R is H or a C$_{1-3}$ aliphatic hydrocarbon radical optionally substituted by one or more carbonyl and/or hydroxy groups, and R' is OH, a C$_{1-3}$ aliphatic hydrocarbon radical or aryl; and wherein the relative concentration of the lytic reagent composition is in an effective amount to effect partitioning of a whole blood sample into a lysed red cell fraction and a leukocyte fraction by (i) causing rapid and essentially complete hemolysis of red blood cells in the blood sample and, (ii) inducing changes in leukocytes in said blood sample to enhance the ability of instrumentation to perform differential analysis and identification of at least five (5) sub-populations of leukocytes.

7. The lytic reagent composition of claim 6, wherein the concentration of the lytic reagent is from about 0.01 to about 1.0 percent by volume.

8. The lytic reagent composition of claim 7, wherein the concentration of the lytic reagent is from about 0.05 to about 0.5 percent by volume.

9. The lytic reagent composition of claim 6, wherein the saponin is in an amount effective to reduce size of the red blood cell fragments so that they will not cause a derivation of an output electrical signal indicative of a species of leukocyte.

10. The lytic reagent composition of claim 6, wherein the saponin is in an amount from about 0.05 to about 0.20% by volume.

11. A lytic reagent composition for selective chemical treatment of a whole blood sample, said lytic reagent composition comprising a differentiation effective amount of a lytic reagent and saponin, wherein said lytic reagent is a carboxylic acid of the formula RCOOH or a sulphonic acid of the formula R'SO$_3$H;

wherein R is H or a $C_{1-3}$ aliphatic hydrocarbon radical optionally substituted by one or more carbonyl and/or hydroxy groups, and R' is OH, a $C_{1-3}$ aliphatic hydrocarbon radical or aryl; and wherein the differentiation effective amount of said lytic reagent composition, when added to a whole blood sample, effecting (i) a decrease in the pH of the sample from its physiological level to a pH in the range of from about 2.6 to about 4.0 while maintaining the osmolality of the fluid at less than about 100 mOs, (ii) rapid and essentially complete hemolysis of the red blood cell fraction in the blood sample, and (iii) changes in the leukocyte cell fraction of the blood sample to enhance the ability of instrumentation to perform differential analysis and identification of at least five (5) sub-populations of leukocytes.

12. The lytic reagent composition of claim 11, wherein the concentration of the lytic reagent is from about 0.01 to about 1.0 percent by volume.

13. The lytic reagent composition of claim 12, wherein the concentration of the lytic reagent is from about 0.05 to about 0.5 percent by volume.

14. The lytic reagent composition of claim 11, wherein the saponin is in an amount effective to reduce the size of red blood cell fragments so that they will not cause a derivation of an output electrical signal indicative of a species of leukocyte.

15. The lytic reagent composition of claim 11, wherein the saponin is in an amount from about 0.05 to about 0.20% by volume.

16. A kit of a lytic reagent system for white blood cell differential analysis comprising:

(a) a lytic reagent composition for selective chemical treatment of a whole blood sample, said composition comprising saponin and a lytic reagent, wherein said lytic is a reagent carboxylic acid of the formula RCOOH or a sulphonic acid of the formula R'SO$_3$H;

wherein R is H or a $C_{1-3}$ aliphatic hydrocarbon radical optionally substituted by one or more carbonyl and/or hydroxy groups, and R' is OH, a $C_{1-3}$ aliphatic hydrocarbon radical or aryl;

wherein the relative concentration of the lytic reagent composition is in an effective amount to effect partitioning of a whole blood sample into a lysed red cell fraction and an essentially intact leukocyte fraction in such a state as to allow differential analysis of at least five populations of such leukocytes; and (b) a quench reagent, said quench reagent being present in sufficient concentration to retard the lytic activity of the lytic reagent composition and restore the physiological environment of the leukocytes within the sample.

17. The kit of claim 16, wherein the concentration of the lytic reagent is from about 0.01 to about 1.0 percent by volume.

18. The kit of claim 16, wherein said quench reagent comprises an alkaline aqueous salt solution containing at least two ingredients selected from the group consisting of sodium chloride, sodium sulfate, sodium carbonate, and sodium bicarbonate.

19. The kit of claim 16, wherein said quench reagent is in an amount effective to stabilize the blood sample at a pH in the range of from about 6 to about 7.5.

20. The kit of claim 19, wherein said saponin is in an amount effective to reduce the size of red blood fragments so that they will not cause a derivation of an output electrical signal indicative of a species of leukocyte.

21. The kit of claim 20, wherein said saponin is in an amount from about 0.05 to about 0.20% by volume.

22. A kit of a lytic reagent system for selective chemical treatment of a whole blood sample comprising: a lytic reagent composition comprising:

(a) a lytic reagent composition comprising saponin and a lytic reagent, wherein said lytic reagent is a carboxylic acid of the formula RCOOH or a sulphonic acid of the formula R'SO$_3$H; wherein R is H or a $C_{1-3}$ aliphatic hydrocarbon radical optionally substituted by one or more carbonyl and/or hydroxy groups, and R' is OH, a $C_{1-3}$ aliphatic hydrocarbon radical or aryl;

wherein the relative concentration of the lytic reagent composition is in an effective amount to effect partitioning of a whole blood sample into a lysed red cell fraction and a leukocyte fraction by (i) causing rapid and essentially complete hemolysis of red blood cells in the blood sample and, (ii) inducing changes in leukocytes in said blood sample to enhance the ability of instrumentation to perform differential analysis and identification of at least five sub-populations of leukocytes, and (b) a quench reagent, said quench reagent being present in sufficient concentration to retard the lytic activity of the lytic reagent composition and restore the physiological environment of the leukocytes within the sample.

23. The kit of claim 22, wherein the concentration of the lytic reagent is from about 0.01 to about 1.0 percent by volume.

24. The kit of claim 22, wherein said quench reagent comprises an alkaline aqueous salt solution containing at least two ingredients selected from the group consisting of sodium chloride, sodium sulfate, sodium carbonate, and sodium bicarbonate.

25. The kit of claim 24, wherein said quench reagent is in an effective amount to stabilize the blood sample at a pH in the range of from about 6 to about 7.5.

26. The kit of claim 25, wherein the saponin is in an amount effective to reduce the size of red blood cell fragments so that they will not cause a derivation of an output electrical signal indicative of a species of leukocyte.

27. The kit of claim 26, wherein the saponin is in an amount from about 0.05 to about 0.20% by volume.

28. A kit of a lytic reagent system for selective chemical treatment of a whole blood sample comprising:

(a) a differentiation effective amount of a lytic reagent and saponin, wherein said lytic reagent is a carboxylic acid of the formula RCOOH or a sulphonic acid of the formula R'SO$_3$H; wherein R is H or a C$_{1-3}$ aliphatic hydrocarbon radical optionally substituted by one or more carbonyl and/or hydroxy groups, and R' is OH, a C$_{1-3}$ aliphatic hydrocarbon radical or aryl; and wherein the differentiation effective amount of said lytic reagent, when added to a whole blood sample, effecting (i) a decrease in the pH of the sample from its physiological level to a pH in the range of from about 2.6 to about 4.0 while maintaining the osmolality of the fluid at less than about 100 mOs, (ii) rapid and essentially complete hemolysis of the red blood cell fraction in the blood sample, and (iii) changes in the leukocyte cell fraction of the blood sample to enhance the ability of instrumentation to perform differential analysis and identification of at least five sub-populations of leukocytes; and (b) a quench reagent, said quench reagent being present in sufficient concentration to retard the lytic activity of the lytic reagent composition and restore the physiological environment of the leukocytes within the sample.

29. The kit of claim 28, wherein the concentration of the lytic reagent is from about 0.01 to about 1.0 percent by volume.

30. The kit of claim 28, wherein said quench reagent comprises an alkaline aqueous salt solution containing at least two ingredients selected from the group consisting of sodium chloride, sodium sulfate, sodium carbonate, and sodium bicarbonate.

31. The kit of claim 30, wherein said quench reagent is in an effective amount to stabilize the blood sample at a pH in the range of from about 6 to about 7.5.

32. The kit of claim 31, wherein the saponin is in an amount effective to reduce the size of red blood cell fragments so that they will not cause a derivation of an output electrical signal indicative of a species of leukocyte.

33. The kit of claim 32, wherein the saponin is in an amount from about 0.05 to about 0.20% by volume.

* * * * *